(12) United States Patent
Bhatia

(10) Patent No.: US 7,527,968 B2
(45) Date of Patent: May 5, 2009

(54) REGENERATION INITIATING CELLS

(75) Inventor: Mickie Bhatia, London (CA)

(73) Assignee: Robarts Research Institute, London, Ontario (CA)

( * ) Notice: Subject to any disclaimer, the term of this patent is extended or adjusted under 35 U.S.C. 154(b) by 63 days.

(21) Appl. No.: 10/523,357

(22) PCT Filed: Jul. 29, 2003

(86) PCT No.: PCT/CA03/01098

§ 371 (c)(1),
(2), (4) Date: Sep. 1, 2005

(87) PCT Pub. No.: WO2004/011012

PCT Pub. Date: Feb. 5, 2004

(65) Prior Publication Data

US 2006/0140913 A1 Jun. 29, 2006

Related U.S. Application Data

(60) Provisional application No. 60/435,294, filed on Dec. 23, 2002, provisional application No. 60/398,791, filed on Jul. 29, 2002.

(51) Int. Cl.
*C12N 5/00* (2006.01)
*C12N 5/02* (2006.01)
(52) U.S. Cl. .................. 435/325; 435/366; 435/372
(58) Field of Classification Search .......... 435/325, 435/366, 372
See application file for complete search history.

(56) References Cited

U.S. PATENT DOCUMENTS

| | | |
|---|---|---|
| 5,780,299 A | 7/1998 | Coon et al. |
| 6,174,526 B1 | 1/2001 | Cerami et al. |
| 2002/0012653 A1 | 1/2002 | Pang et al. |
| 2003/0082155 A1 * | 5/2003 | Habener et al. .......... 424/93.21 |

FOREIGN PATENT DOCUMENTS

| | | |
|---|---|---|
| EP | 1 254 952 A | 11/2002 |
| WO | WO 01 11011 A2 | 2/2001 |
| WO | WO 01/21766 A2 | 3/2001 |
| WO | WO 01/21767 A2 | 3/2001 |
| WO | WO 02/09650 A2 | 2/2002 |
| WO | WO 02/13760 A2 | 2/2002 |
| WO | WO 02 064748 A2 | 8/2002 |
| WO | WO 02 083187 A | 10/2002 |

OTHER PUBLICATIONS

Hess, David et al., Bone marrow-derived stem cells initiate pancreatic regeneration, Nature Biotechnology, 21(7), pp. 763-770, 2003, XP002265780.
Ortiz, Mariaestela et. al., Functional characterization of a novel hematopoietic stem cell and its place in the c-kit maturation pathway in bone marrow cell development, Immunity, 10(2), pp. 173-182, 1999, XP001156831.
Springer, Matthew L. et al., Not the usual suspects: the unexpected sources of tissue regeneration, Journal of Clinical Investigation, 107(11), pp. 1355-1356, 2001, XP002265781.
Tsai, Robert Y. L. et al., Plasticity, niches, and the use of stem cells, Developmental Cell, 2(6), pp. 707-712, 2002, XP009023173.
Beilhack, George F. et al., Purified allogenic hematopoietic stem cell transplantation blocks diabetes pathogenesis in NOD mice, Database CA 'Online!, Chemical Abstracts Service, Columbus, OH, Database accession No. 139:875 CA, XP002265783. Abstract & Diabetes (2003), 52(1), pp. 59-68, 2003.
Ende, Norman et al., NOD/LtJ type I diabetes in mice and the effect of stem cells (Berashis) derived from human umbilical cord blood, Database Biosis 'Online!, Biosciences Information Service, Philadelphia, PA, Database accession No. PREV200300399271, XP002265784. Abstract & Journal of Medicine, vol. 33, No. 1-4, 2002, pp. 181-187, ISSN: 0025-7850.
Ikehara, S. et. al., Prevention of type I diabetes in nonobese diabetic mice by allogeneic bone marrow transplantation, Proc. Natl. Acad. Sci, USA 82, 7743-7747, 1985.
Than, S. et. al., Journal of Exp. Med., 176(40, 1233-1238, 1992.

\* cited by examiner

*Primary Examiner*—Ruth A Davis
(74) *Attorney, Agent, or Firm*—Pabst Patent Group LLP

(57) ABSTRACT

Methods and compositions for treating hyperglycemia and pancreatic damage as well as stimulating the repair or regeneration of islet cells are disclosed.

9 Claims, 7 Drawing Sheets c  Frequency of PECAM-1+ donor endothelial cells in the pancreas of NOD/SCID recipients

|  | BM Transplanted | |
|---|---|---|
| STZ | − | + |
| Total donor cells (GFP+) | 177 | 316 |
| Total PECAM+ donor cells (PECAM+/GFP+) | 1 | 29 |
| Frequency of PECAM+ donor cells (%) | 0.6 | 9.2 |

REGENERATION INITIATING CELLS

This application is a filing under 35 USC §371 of PCT/CA2003/001098, filed in the Canadian Receiving Office of the Patent Cooperation Treaty on Jul. 29, 2003, which claims priority to U.S. Ser. No. 60/398,791, filed in the U.S. Patent and Trademark Office on Jul. 29, 2002 and U.S. Ser. No. 60/435,294, filed in the U.S. Patent and Trademark Office on Dec. 23, 2002.

FIELD OF THE INVENTION

The present invention relates to methods and compositions comprising regeneration initiating cells for the treatment of hyperglycemia, for the treatment or prevention of pancreatic damage and for stimulating the repair or regeneration of islet cells. The methods are useful in the treatment of diabetes.

BACKGROUND OF THE INVENTION

Until recently, the ability to differentiate into multiple tissue types was traditionally a property reserved to embryonic stem cells (8-10). Recent studies have demonstrated that tissue specific stem cells, thought to have restricted differentiation potential to the tissue from which they were derived, are capable of producing cellular phenotypes of alternative tissue upon transplantation (11,12). This cellular property of stem cells has been termed "transdifferentiation" (8). A principal example of these observations comes from transplantation of bone marrow (BM) derived stem cells that have generated unexpected phenotypes in vivo that include muscle (2-4), liver (6), brain (1,13), and cells of epithelial lineage (5). These studies suggest that the existence of an active pool of stem cells can be procured from the BM compartment that are capable of either transdifferentiation or represent less restricted cells with multiple tissue differentiation potential. In the context of regenerative therapies, adult stem cells with these properties has ignited the hope of obtaining a source of stem cells with pluripotent potential (14), thereby avoiding the necessity of obtaining human embryonic stem cells for tissue/organ repair.

Bone marrow derived stem cells have been reported by many groups (40; WO 02/13760; WO 02/09650; WO 01/21766; WO 01/21767; U.S. Pat. No. 6,174,526; and US 2002/0012653). Ikehara at al. (40) relates to the reconstitution of irradiated NOD mice with bone marrow cells from BALB/c nu/nu mice to treat insulitis or diabetes. Than et al. (41) demonstrated that allogenic bone marrow transplantation could be used to treat non-insulin-dependent diabetes in mice and could promote morphological recovery of islets.

Although BM derived stem cells have demonstrated trans- or multipotent differentiation into damaged tissue, the restoration of physiological function and implied benefit to the recipients have rarely been demonstrated (6,7). Since identification of donor cells adopting alternative tissue phenotypes alone does not adequately determine the therapeutic viability of stem cell engraftment, more recent studies have associated the number of transdifferentiating donor cells observed to liver (6) or cardiac function (7). However, the low frequency of donor cell chimerism, together with an almost complete restoration of tissue function (7), illustrates an enigmatic dichotomy between stem cell contribution and physiological recovery that has yet to be resolved.

SUMMARY OF THE INVENTION

The present inventor has isolated low density mononuclear cells from bone marrow that can rescue hyperglycemia and augment pancreatic repair and generation of endogenous islet cells in animals with pancreatic damage causing diabetes.

The cells, which are termed regeneration initiating cells (RICs), are distinguished from stem cells of the prior art in many respects. First, the RICs are capable of rescuing hyperglycemia in a diabetic animal, and such capability has not been reported for stem cells. Second, the RICs only differentiate and induce endogenous repair in the presence of damaged cells or organs. In particular, the inventor has shown that animals given RICs without pancreatic damage displayed no donor derived cells in the pancreas and no endogenous beta cells were formed. In contrast, in animals with pancreatic damage the RICs differentiated into epithelial cells in the pancreas and there was increased generation of endogenous islet cells. Third, the RICs home to the site of damage and do not have to be administered locally. Fourth, the RICs can be isolated directly from bone marrow and do not need to be cultured. In contrast, the stem cells described in the prior art require in vitro culture before they display their stem cell properties.

Accordingly, the present invention provides a method of preventing or treating pancreatic damage comprising administering an effective amount of a regeneration initiating cell to an animal in need thereof.

The invention also provides a method of stimulating the repair or regeneration of endogenous islet cells comprising administering an effective amount of a regeneration initiating cell to an animal in need thereof.

The present invention also provides a method of inducing the repair or regeneration of a damaged insulin secreting cell comprising administering an effective amount of a regeneration initiating cell to an animal in need thereof.

The present invention further provides a method for treating hyperglycemia comprising administering an effective amount of a regeneration initiating cell to an animal in need thereof.

The regeneration initiating cell is preferably derived from a human bone marrow, human peripheral mobilized blood or human cord blood cells.

The invention also provides a pharmaceutical composition for treating and preventing pancreatic damage comprising an effective amount of a regeneration initiating cell in admixture with a pharmaceutically acceptable diluent, excipient or carrier.

The present invention also includes a pharmaceutical composition for stimulating the repair or regeneration of islet cells comprising an effective amount of a regeneration initiating cell in admixture with a pharmaceutically acceptable diluent, excipient or carrier.

The present invention further includes a pharmaceutical composition for inducing the regeneration or repair of a damaged insulin secreting cell comprising an effective amount of a regeneration initiating cell in admixture with a pharmaceutically acceptable diluent, excipient or carrier.

The present invention also includes a pharmaceutical composition for treating hyperglycemia comprising an effective amount of a regeneration initiating cell in admixture with a pharmaceutically acceptable diluent excipient or carrier.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Therapeutic Methods

Figure 1:
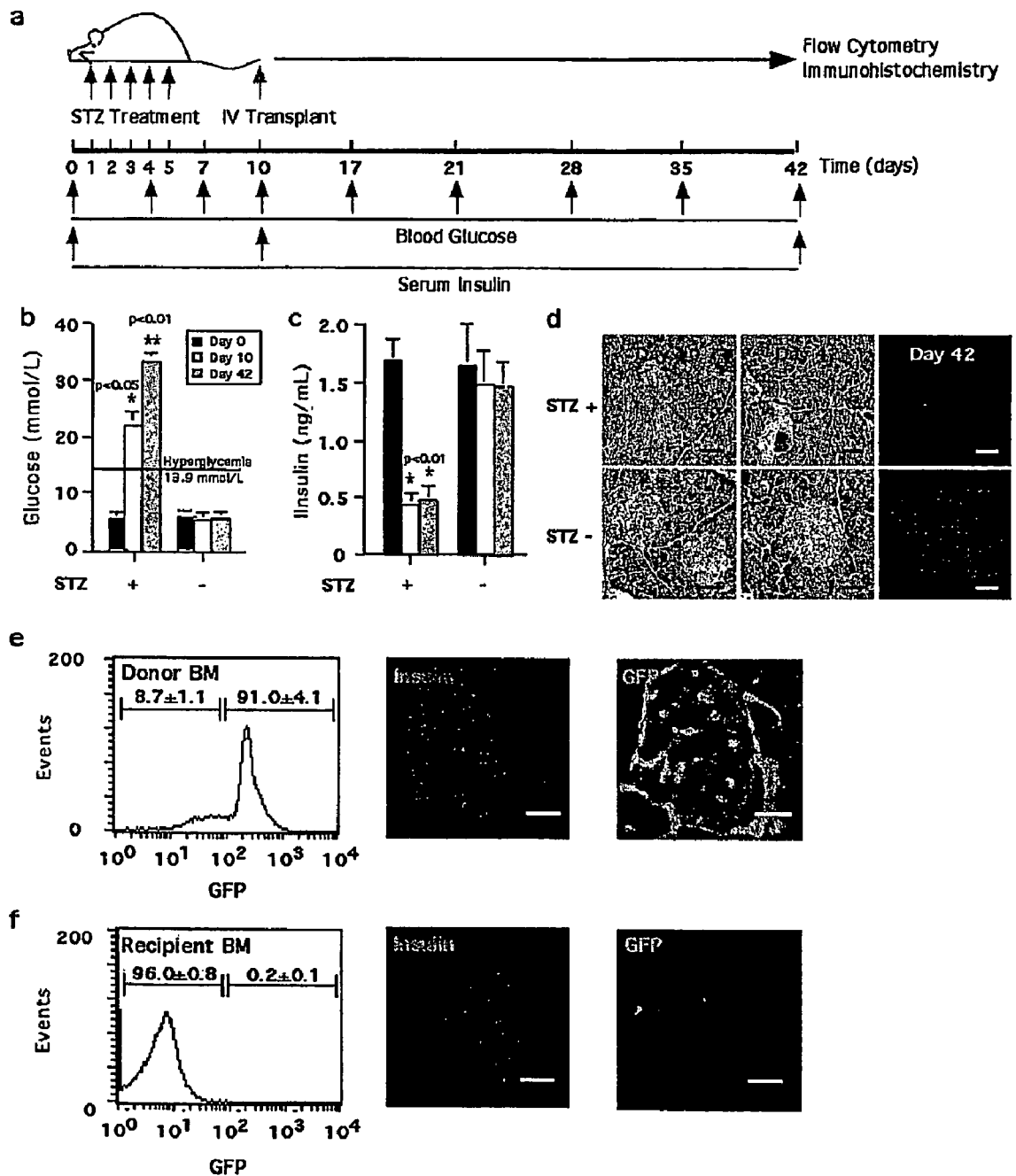
FIG. 1 shows pancreatic damage and induction of hyperglycemia after STZ treatment in NOD/SCID mice. a, In vivo model for the induction of hyperglycemia and transplant of GFP/FVB BM cells into streptozotozin (STZ)-injected NOD/SCID mice. b, IP injection of STZ (n=12) (35 mg/kg/day); or citrated buffer vehicle (n=9) for 5 days followed by sub-lethal irradiation (350 cGy) and mock transplant (PBS) at day 10 produced elevated blood glucose from day 10 through day 42. c, Increased blood glucose correlated with decreased systemic insulin measured in identical mice at day 10 and 42. Data are shown as mean±S.E.M. d, H and E staining and immunofluorescence of pancreatic sections at 10 and 42 days after STZ-treatment. STZ-treated mice demonstrated reduced number of islets, altered islet morphology and the absence of insulin production. e, f, Flow cytometry and immunofluorescence of insulin and GFP expressing cells in the BM and pancreas of donor (GFP/FVB, n=4) and recipient (NOD/SCID, n=3) mice. Scale bars=50 mm.

The inventor has shown that intravenous transplantation of regeneration initiating cells (RICs) rescued hyperglycemia in streptozotozin induced diabetic mice. Marked reduction of serum glucose occurred concomitantly with insulin production, and was restricted to the transplanted cells expressing the stem cell marker c-kit. In the pancreas, although a low frequency of donor cells expressed insulin, the majority surrounded ductal and islet regions, and expressed the endothelial marker PECAM-1. Corrected mice possessed a greater number of islets and insulin positive cells; however these were shown to be primarily of recipient origin. The results demonstrate that transplantation of regeneration initiating cells augments pancreatic repair and generation of endogenous islets, thereby providing evidence for a novel mechanism by which regeneration initiating cells contribute to restoration of tissue function. Therefore, the transplantation of regeneration initiating cells can indirectly assist in the regeneration and repair of endogenous tissues or organs in the recipient without requiring that the regeneration initiating cells differentiate into the cell type to be regenerated. The inventor has also shown that the regeneration initiating cells do not induce the regeneration or repair of cells that are not damaged. This feature makes RICs extremely useful as therapeutic agents as they only function in situations where repair is necessary or desired. Healthy cells will not be induced to regenerate. The inventor has isolated regeneration initiating cells from both murine and human sources.

Accordingly, the present invention further includes a method of inducing the regeneration or repair of a damaged tissue or organ comprising administering an effective amount of a regeneration initiating cell to an animal in need thereof.

The damaged tissue or organ can be any tissue or organ that become damaged by either infection or congenital disease or injury. These tissues/organs include, but are not limited to, pancreas, liver, neural, cardiac, skeletal and smooth muscle, endothelium, cartilage, kidney, and epithelium.

In one embodiment, the present invention provides a method of treating or preventing pancreatic damage comprising administering an effective amount of a regeneration initiating cell to an animal in need thereof. The present invention also includes a use of an effective amount of a regeneration initiating cell for the manufacture of a medicament for treating or preventing pancreatic damage.

In another embodiment, the present invention also provides a method of stimulating the repair or regeneration of endogenous islet cells comprising administering an effective amount of a regeneration initiating cell to an animal in need thereof. The invention also includes a use of an effective amount of a regeneration initiating cell for the manufacture of a medicament for stimulating the regeneration or repair of damaged islet cells.

In yet another embodiment, the present invention further includes a use of an effective amount of a regeneration initiating cell for the manufacture of a medicament for stimulating the regeneration or repair of a damaged insulin secreting cell. The present invention also includes a use of an effective amount of a regeneration initiating cell for the manufacture of a medicament for stimulating the regeneration or repair of a damaged insulin secreting cell.

The term "effective amount" as used herein means an amount effective, at dosages and for periods of time necessary to achieve the desired result (e.g. to treat or prevent pancreatic damage, to repair or regenerate endogenous islet cells). For example, in one embodiment an effective amount of RICs can correlate to dosages disclosed in Grewal et al., 2003 for CBT (i.e. $1.5 \times 10^7$ cells/Kg as mononuclear cells and $1.7 \times 10^5$ cells/Kg as CD34⁻ positive cells).

The term "animal" as used herein includes all members of the animal kingdom, including humans. Preferably, the animal to be treated is a human, most preferably a human with diabetes.

The term "stimulating the regeneration or repair" of a particular damaged organ, tissue or cell type means that the regeneration initiating cells augment, assist or induce the repair as compared to the state of the organ, tissue or cell type in the absence of the regeneration initiating cells.

The term "regeneration initiating cell" or "RIC" as used herein means a low density mononuclear cell which can be isolated directly from a biological source (such as bone marrow or cord blood) without culturing, and can home into damaged organs/tissues (such as pancreas) and initiate regeneration of the organs/tissues by inducing differentiation of endogenous stem/progenitor cells to the lost-type or damaged functional cells without differentiating to said cells by themselves.

The regeneration initiating cell preferably contains the marker stem cell factor receptor, c-kit. The regeneration initiating cell may also contain one or more of the markers KDR, AC133, CD34, Tie-1/2, Tek-1/2, VEGF-receptor families, CD31, and angiopoietin receptors.

The regeneration initiating cell can be obtained from a variety of sources including, but not limited to, peripheral blood, bone marrow, umbilical cord cells (including umbilical vein endothelial cells) as well as embryonic cells or placenta. Preferably, the regeneration initiating cell is derived from cord blood, adult bone marrow or peripheral blood. The source of cells can be freshly obtained or can be obtained from previously frozen samples. The regeneration initiating cell can be derived from any animal and is preferably from a mammal such as a rodent or a human, most preferably a human. The regeneration initiating cells used in the methods of the invention may be patient derived (autologous) or from a donor (allogeneic).

The term "a cell" as used herein includes a single cell as well as a plurality of population of cells. Administering a regeneration initiating cell includes administering cells that have been prepared or expanded in vitro as well as expanding or stimulating regeneration initiating cells that are present in the animal in vivo.

Preferably, the regeneration initiating cells are prepared and expanded in vitro prior to administration to the animal. The regeneration initiating cells can be isolated from adult bone marrow or peripheral blood using techniques known in the art (see WO 01/11011) or described in Example 1 or from human cord blood as described in Example 2. Briefly, low density mononuclear cells (LDMNC) may be isolated by gradient centrifugation. The LDMNC may be used directly as a source for regeneration initiating cells or the regeneration initiating cells may be further purified from the LDMNC using positive or negative selection methods. In positive selection, the regeneration initiating cells can be isolated using antibodies that bind to regeneration initiating cell markers such as c-kit, KDR, AC133, CD34, Tie-1/2, Tek-1/2, VEGF-receptor families, CD31, and angiopoietin receptors. In negative selection, cells that are not regeneration initiating cells can be removed from the LDMNC using antibodies that bind to non-regeneration initiating cell markers such as CD3, CD4 and CD8. Using either method the isolated regeneration initiating cells can be cultured in serum free conditions containing minimal essential amino acids, insulin, transferrin and serum albumin prior to transplantation in vivo if an expansion of RIC is required.

The regeneration initiating cells can be administered to the animal using a variety of techniques including systemically or directly at the site of a tissue or organ, such as the pancreas. The regeneration initiating cell may be administering intravenously or by portal vein injection.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treating" can also mean prolonging survival as compared to expected survival if not receiving treatment.

The present inventor has shown that transplantation of regeneration initiating cells into diabetic mice rescued the hyperglycemia in the mice. Accordingly, the present invention provides a method of treating hyperglycemia comprising administering an effective amount of a regeneration initiating cell to an animal in need thereof. The present invention also provides a use of an effective amount of a regeneration initiating cell for the manufacture of a medicament for treating hyperglycemia.

The term "treating hyperglycemia" means that the glucose levels in the animal receiving the regeneration initiating cells will be reduced as compared to the glucose levels in an animal not receiving the regeneration initiating cells. Glucose levels can be measured using techniques known in the art. For example, blood glucose levels may be measured with a glucometer such as the Elite® diabetes care system from Bayer, Germany.

In a preferred embodiment, the animal to be treated is a hyperglycemic human with diabetes. Accordingly, the present invention provides a method of treating diabetes comprising administering an effective amount of a regeneration initiating cell to a diabetic animal.

II. Compositions

The present invention also includes pharmaceutical compositions for carrying out the therapeutic methods of the invention. In one aspect, the present invention provides a pharmaceutical composition for treating or preventing pancreatic damage comprising an effective amount of the regeneration initiating cell in admixture with a pharmaceutically acceptable diluent, excipient or carrier. In another aspect, the present invention includes a pharmaceutical composition for stimulating the regeneration or repair of damaged islet cells comprising an effective amount of the regeneration initiating cell in admixture with a pharmaceutically acceptable diluent, excipient or carrier. In a further embodiment, the present invention provides a pharmaceutical composition for inducing the regeneration or repair of a damaged tissue or organ comprising an effective amount of a regeneration initiating cell in admixture with a pharmaceutically acceptable diluent or carrier. The invention also includes a pharmaceutical composition for inducing the regeneration or repair of a damaged insulin secreting cell comprising an effective amount of a regeneration initiating cell in admixture with a pharmaceutically acceptable diluent, excipient or carrier. The invention also includes a pharmaceutical composition for treating hyperglycemia comprising an effective amount of the regeneration initiating cell in admixture with a pharmaceutically acceptable diluent or carrier.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example gelatin capsules, capsules, suppositories, soft gelatin capsules, gels, membranes, tubelets, solutions or suspensions.

The pharmaceutical compositions of the invention can be intended for administration to humans or animals. Dosages to be administered depend on individual needs, on the desired effect and on the chosen route of administration. For example, pharmaceutical composition comprising an effective amount of RIC cells can be administered. This can be administered in one dose or multiple doses depending on the treatment protocol.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as agents that are useful in treating hyperglycemia and/or treating or preventing pancreatic damage and/or stimulating the repair or regeneration of islet cells.

III. Method of Detecting RIC Cells

The present invention also includes a method or assay system for determining whether or not regeneration initiation cells are present in a biological sample.

Accordingly, the present invention also provides a method of detecting the presence of a regeneration initiation cell in a sample comprising:

(a) isolating low density mononuclear cells from the sample;

(b) transplanting the low density mononuclear cells into a recipient animal with tissue or organ damage; and (c) determining whether or not the transplanted cells engraft the damage tissue or organ, wherein engraftment of the damaged tissue or organ indicates the presence of regeneration initiation cells in the sample.

The sample used in the assay can be any sample that contains low density mononuclear cells such as peripheral blood, bone marrow, umbilical cord cells as well as embryonic cells or placenta. Preferably, the sample is human cord blood, adult bone marrow or adult peripheral blood. The low density mononuclear cells may be isolated from the sample using techniques known in the art such as gradient centrifugation as described in the examples. Prior to transplanting the low density mononuclear cells, they can be further purified to enrich for the regeneration initiation cells. For example, the cells may be sorted and cells containing the markers c-kit can be selected as described in Example 1. The cells can also be further sorted based on additional markers including KDR, AC133, CD34, Tie-1/2, Tek-1/2, VEGF-receptor families, CD31, and angiopoietin receptors.

The recipient animal can be any animal, preferably non-human, that has tissue or organ damage. In one embodiment, the animal is a mouse with diabetes such as the NOD/SCID mice treated with streptozotozin as described in Example 1.

The following non-limiting example is illustrative of the present invention:

EXAMPLES

Example 1

Bone Marrow Derived Regeneration Initiating Cells Rescue Hyperglycemia by Regeneration of Recipient Islets Methods Induction of Hyperglycemia and Blood Glucose Monitoring 8-10 week old, immune deficient NOD/SCID mice (Jackson Laboratories, Bar Harbor, Mass.) were injected with 35 mg/kg streptozotocin (STZ) (Sigma-Aldrich, Oakville, ON) daily for days 1-5. STZ was solubilized in citrate buffer pH 4.5 and injected within 15 minutes of preparation. Blood glucose was measured between 8-10 am, twice weekly from days 0-14 and weekly from days 14-42 with a glucometer Elite® diabetes care system (Bayer). Peripheral blood (100 µL) was collected on days 0, 10 and 42 and serum insulin was quantified using an $^{125}$I-labelled murine insulin-specific radio-immuno assay kit (Linco). For the in vivo detection of proliferating cells in the pancreas of recipient NOD/SCID mice, BrdU (50 µg/kg body weight in PBS, Sigma) was IP injected 16 and 2 hours prior to pancreas extraction. NOD/SCID mice were maintained under sterile conditions in micro-isolator cages in ventilated racks and treatment protocols were approved by the animal care and ethics committee at the University of Western Ontario.

Transplantation of Hyperglycemic Mice

The BM cells from Green Fluorescent Protein (GFP) expressing transgenic Friend leukemia virus B (FVB) mice (37) were extracted from the tibiae, femurs and iliac crest and isolated (LD) MNCs obtained by gradient centrifugation were transplanted by tail vein injection into sub-lethally irradiated (350 cGy), STZ-treated or untreated NOD/SCID mice according to standard protocols. GFP$^+$ BM cells were transplanted de novo or irradiated (1500 cGy) prior to transplant in order to arrest their proliferative capacity. GFP expressing c-kit$^-$ and c-kit$^+$ cells were directly purified at high speed by staining with anti-CD117-APC (c-kit) antibody (Beckton Dickinson) and sorted using fluorescence activated cell sorter (FACS Vantage SE) and CellQuest™ software (BD). Sorting gates were established on GFP+ BM cells stained with fluorochrome conjugated IgG1 as isotype (BD). c-kit$^+$ and c-kit$^-$ cells were also plated into methocult™ GF M3434 semisolid media (Stem Cell Technologies) and assayed for in vitro clonogenic progenitor capacity as described previously (38). Colony formation was enumerated by light microscopy following incubation for 14 days.

Flow Cytometry of Murine BM and Pancreas

BM cells were harvested from the tibiae, femurs and iliac crest of transplanted mice and the proximal portion of each pancreas was harvested and mechanically separated into a single cell suspension. Approximately $10^6$ murine BM or pancreas cells were stained with 7-AAD viability dye (Beckman Coulter) and analyzed for GFP expressing donor cells on a FACS Calibur cytometer (BD). For multilineage analysis of hematopoietic cell surface markers, BM or pancreas cells were incubated with murine pan-leukocyte-specific marker anti-CD45-APC in combination with anti-CD3-PE, anti-NK1.1-PE, anti-Mac-PE, anti-Gr-1-PE or isotype matched controls (all antibodies from BD) and analyzed after gating for GFP$^+$ donor cells.

Pancreatic Insulin

Pancreata were removed from the mice and insulin was extracted by mechanical homogenization in the presence of 1 mL acid ethanol (165 mM Hcl/75% ethanol). After 18 h incubation at 4° C., insulin was quantified in the supernatant by radioimmunoassay (Linco) and normalized per mg pancreatic tissue (39).

Immunohistochemistry

The distal portion of pancreatic tissues were fixed overnight in 10% buffered formalin, incubated with 30% sucrose in 0.1M PBS at 4° C. and embedded in frozen tissue embedding gel (Fisher). Serial sagital cryosections were cut at a thickness of 5 µm and spanned approximately 760 µm of the distal region of the pancreas. Mounted sections were also immuno-stained with mouse anti-insulin (1:2000, Sigma), rat anti-PECAM-1 (CD31)(1:20, BD), rabbit anti-Mac-1 (CD11b)(1:10, BD), rabbit anti-GFP (1:20 Santa Cruz) or isotype matched control antibodies. Labeled cells were visualized using a biotin conjugated secondary antibody with a streptavidin-Texas red system (Vector Laboratories). Isotype-matched antibodies and PBS were used as control for stained sections. Nuclear regions were stained with 4,6 diamidino-2-phenylindole (DAPI) counter-staining (Vector). Images were collected with an Olympus confocal laser-scanning microscope.

Histomorphometry

Sections from each transplanted mice were stained with hematoxylin and eosin (HE) to examine pancreatic islet morphology after STZ-treatment and subsequent transplantation. Islet size and number were scored using an Olympus light microscope IX50 and a computer-assisted image analysis program (Image Pro Plus 4.5).

RT-PCR Analysis

Unprocessed cells from the pancreas of transplanted chimeric mice were sorted for GFP$^+$ (donor) and GFP$^-$ (recipient) cells using a FACS Vantage SE cytometer and flash frozen in liquid nitrogen. mRNA was extracted using Quick-Prep micro mRNA purification kit and cDNA was synthesized using first strand cDNA synthesis kit (Amersham Pharmacia). PDX-1 specific sequences were amplified by PCR (GeneAmp@ PCR System 9700, Perkin Elmer) using the primers PDX-1-Forward, 5' CCA CAC AGC TCT ACA AGG ACC 3' (SEQ ID NO: 1) and PDX-1-Reverse, 5' CGT TGT CCC GCT ACT ACG TTT C 3' (SEQ ID NO: 2) and beta actin-P1, 5' GATCCACATCTGCTGGAAGG 3'(SEQ ID NO: 3) and P2, 5' AAGTGACGTTGACAT CCG 3' (SEQ ID NO: 4).

Statistics

Blood glucose and serum insulin concentrations were shown as the mean±standard error of the mean (S.E.M.) for mice grouped according to transplanted cell populations or mock (PBS) injection. Statistical analysis for significance was performed by a two-tailed Student's t-test.

Results

To determine the cellular mechanism and physiological relevance of BM derived regeneration initiating cells to restore tissue function, the inventor has adopted a murine model of chemically induced pancreatic damage that causes diabetes in recipients (15). Using streptozotozin (STZ) induced diabetic recipients, together with donor GFP expressing BM cells from transgenic mice; the inventor designed an experimental approach outlined in FIG. 1a. Immune-deficient recipients were treated for 5 days with 35 mg/kg/day of STZ with 5 consecutive daily injections beginning at Day 1. As shown in FIG. 1b, by day 10, 100% of the treated mice were hyperglycemic (blood glucose>13.9 mmol/L) and were intravenously transplanted with GFP derived bone marrow from allogenic donors. Blood glucose and serum insulin were monitored throughout the experiment at times indicated (FIG. 1a).

By day 42, blood glucose levels elevated above 30 mmol/L (FIG. 1b) and as many as 40% of animals either died or had to be sacrificed (data not shown). Increased blood glucose levels correlated with drastic reductions in serum insulin observed by day 10, that remained attenuated at day 42 compared to untreated controls (FIG. 1c). Reduction in serum insulin was directly associated with the initial destruction of pancreatic islets at day 10 and eventual absence of detectable islets at day 42 compared to control untreated mice detected by morphological assessment of Hematoxalin and Eosin (H+E) and insulin specific antibody stained pancreatic sections (FIG. 1d). The absence of mature hematopoietic cells (CD3+ T-cells, NK+ natural killer cells, MAC-1+ macrophage, and GR-1+ granulocytes, data not shown) in the pancreas of NOD/SCID mice before or after STZ treatment confirmed the mechanism of STZ induced islet damage and secondary hyperglycemia is not mediated through autoimmune response.

Upon establishing a reliable model that provided physiological indices associated with tissue damage such as blood glucose and serum insulin, the inventor sought to examine the function of transplanting BM derived regeneration initiating cells from transgenic GFP expressing donors. By FACS analysis, greater than 90% of BM mononuclear cells expressed GFP in transgenic mice transcribing GFP by the ubiquitin promoter (FIG. 1e). In addition, tissue sections of the pancreas of GFP mice indicated that pancreatic islet cells producing insulin expressed GFP as detected by confocal laser scanning microscopy (FIG. 1e). In contrast, untreated NOD/SCID recipients were devoid of GFP+ cells in the BM and although the islets could be observed in pancreatic sections, no background fluorescence of GFP specific emissions were detected (FIG. 1f).

Figure 2:
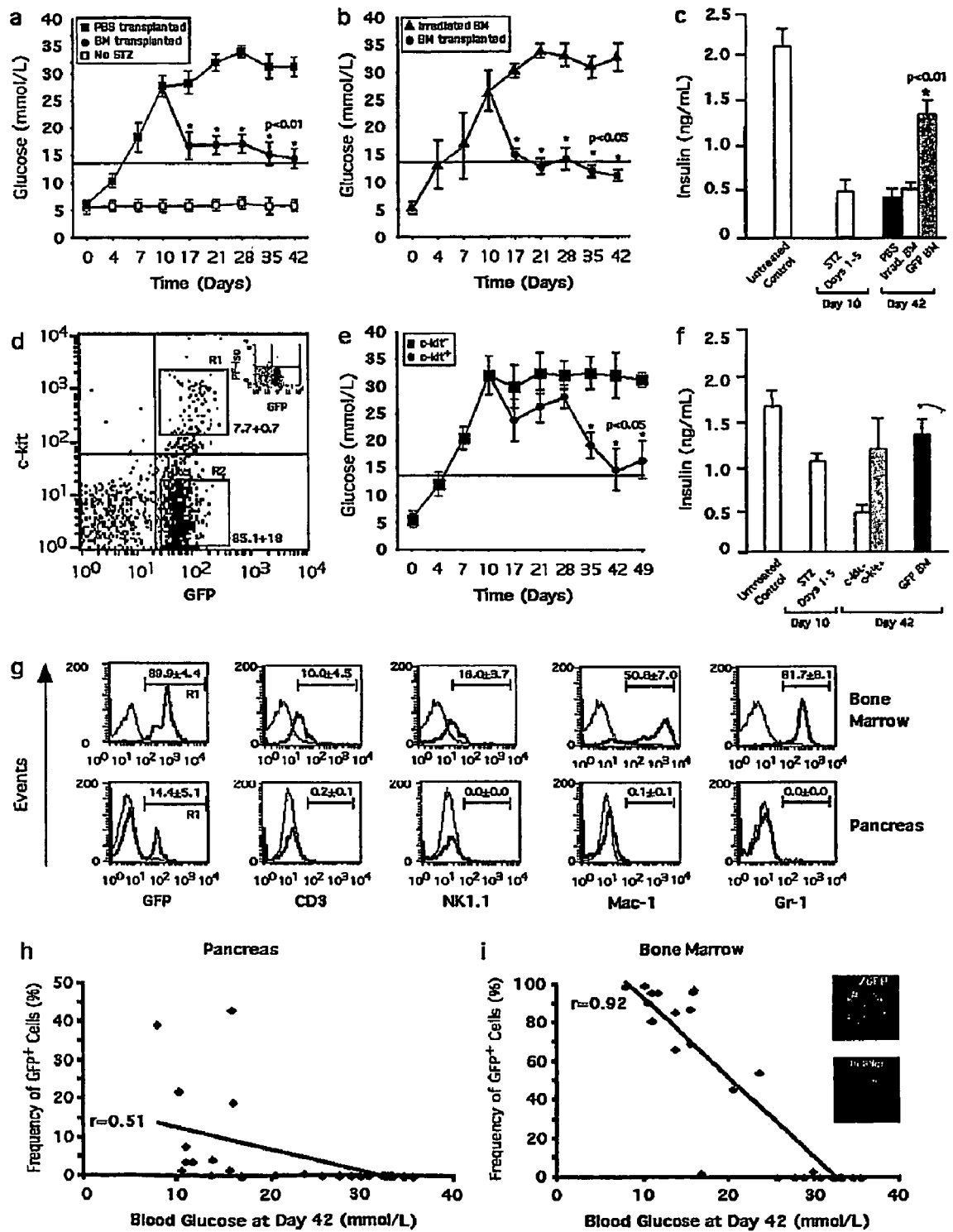
FIG. 2 shows correction of elevated blood glucose in STZ-treated NOD/SCID mice after transplant with functional whole BM or purified c-kit expressing BM derived cells. a, b, Comparison of blood glucose in STZ-treated mice transplanted with GFP/FVB BM cells (●. n=7), irradiated GFP/FVB BM cells (▲, n=3), or PBS, (■, n=5) transplanted. Blood glucose in mice not treated with STZ (□, n=11) remained normal. Permanent correction of elevated blood glucose occurred within 7 days after transplant of GFP/FVB BM cells. c, Correction of blood glucose correlated with increased systemic insulin measured in identical mice. d, Flow cytometry for the isolation of purified c-kit$^+$ (R1) and c-kit$^-$ (R2) donor BM cells from GFP/FVB mice. e, Comparison of blood glucose in STZ-treated mice transplanted with GFP/FVB BM c-kit$^+$ cells (●, n=6), or c-kit– cells (■, n=5). Permanent correction of elevated blood glucose occurred 25 days after the transplant of GFP/FVB BM c-kit$^+$ cells. f, Correction of blood glucose correlated with increased systemic insulin measured in identical mice. All glucose and insulin data are shown as mean±S.E.M. g, Flow cytometry of cells isolated from the BM (n=3) and pancreas (n=3) of STZ-treated NOD/SCID mice transplanted with GFP BM cells. GFP$^+$ reconstituting cells in the pancreas were devoid of cells expressing mature hematopoietic markers. Light line=isotype control, dark line=specific antibody. h, i, Correlation of blood glucose correction with the frequency of GFP$^+$ cells in the BM and pancreas of recipient mice (n=25). Insets demonstrate the presence of GFP$^+$ cells in the BM that do not produce insulin.

Mice treated with STZ demonstrated elevated blood glucose levels between 25-30 mmol/L by day 10, in contrast to control groups of mice injected with citrate buffer (used as the carrier for STZ) that maintained normal glucose levels for the entire experimental period (FIG. 2a). At day 10, STZ induced diabetic mice were randomly separated into 2 groups; one receiving mock intravenous transplants of PBS, and the other receiving whole BM harvested from GFP transgenic donors (FIG. 2a). By day 17, blood glucose levels were markedly reduced in diabetic mice transplanted bone marrow and continued to be suppressed to day 42, whereas animals transplanted with PBS showed no alteration in the initially elevated blood glucose and remained hyperglycemic (FIG. 2a). To evaluate whether transplanted BM cells were secreting factors capable of controlling glucose levels in vivo, similar experiments were performed where hyperglycemic mice were transplanted with irradiated BM cells. Irradiated BM cells have previously been shown to become senescent, while maintaining survival and active secretion of soluble factors and membrane expressed proteins (16). Similar to previous results, mice transplanted with whole BM showed marked decrease in blood glucose levels at day 17 to day 42; however, diabetic animals intravenous (IV) transplanted with irradiated BM did not show any reduction in blood glucose (FIG. 2b), similar to PBS transplanted mice (FIG. 2a). Untreated control mice showed normal levels of serum insulin at day 0, whereas by day 10, serum insulin levels were reduced in mice treated with STZ (FIG. 2c). Neither PBS nor irradiated BM transplantation were able to restore serum insulin levels, whereas mice transplanted with whole BM demonstrated complete recovery (FIG. 2c). The results indicate mitotically active BM cells are able to reduce levels of blood glucose and elevate levels of serum insulin in diabetic recipient mice having undergone pancreatic tissue damage.

To determine the nature of cells residing in the BM compartment capable of rescuing hyperglycemia in diabetic recipients, BM mononuclear cells from GFP mice were divided into subpopulations of cells expressing or lacking the regeneration initiating cell marker, c-kit (17,18). Viable 7AAD excluding cells (R1, not shown) were gated and sorted into c-kit$^-$ (R2) and c-kit$^+$ (R3) subsets (FIG. 2d) at >96% purity. C-kit- and c-kit+ BM cells were transplanted by IV transplantation into STZ induced diabetic mice (FIG. 2e). Diabetic mice transplanted with c-kit$^-$ cells at cell doses of $2\times10^6$ cells were unable to alter hyperglycemia. In contrast, mice transplanted with as few as $1\times10^5$ c-kit$^+$ cells (20 fold less than the number of c-kit$^-$ cells) showed marked reduction in blood glucose levels by days 28 to 35 and eventually decreased to levels similar to reductions achieved using whole BM (FIG. 2e). The delay of blood glucose reduction, compared to unpurified BM cells, is reminiscent of delayed hematopoietic reconstitution using highly purified hematopoietic regeneration initiating cells (18). Similar to the effects of whole BM transplantation (FIGS. 2a,b), c-kit$^+$ cells were able to increase serum insulin levels by day 42-49, that correlated with the drastic reduction in blood glucose levels, whereas transplantation of c-kit$^-$ cells had no effect on physiological state of diabetic mice (FIG. 2f). The results indicate that c-kit$^+$ cells derived from the BM compartment are capable of restoring serum insulin and controlling blood glucose, suggesting that primitive BM regeneration initiating cells are responsible for correction of hyperglycemia.

Figure 3:
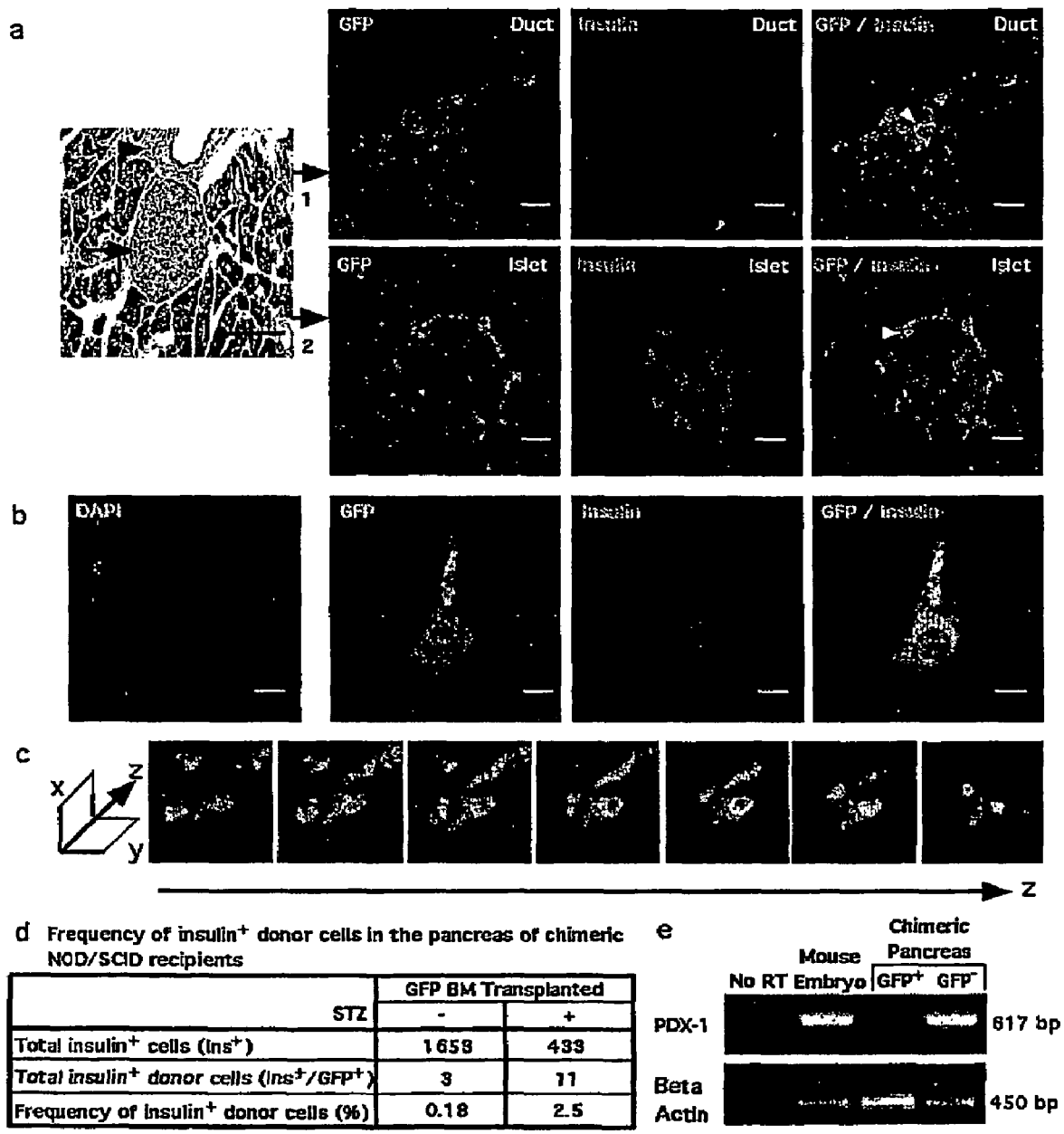
FIG. 3 shows that transplanted BM derived cells engraft surrounding ductal and islet regions in recipient pancreas and produce low frequency of donor insulin positive cells devoid of PDX-1 expression. a, GFP and insulin expression of donor cells engrafting the ductal epithelial region and surrounding recipient-derived insulin producing cells. Arrowheads indicate insulin producing donor cells located in each region. b, Visualization of insulin producing donor (insulin$^+$/GFP$^+$) cell. c Z-series of a single insulin producing donor cell. Arrowheads indicate cytoplasmic staining of insulin granules with GFP expression throughout the nuclear and cytoplasmic regions. Each panel represents serial images (5 µm) through the thickness of the section. d, Frequency of insulin producing donor cells in the chimeric pancreas of NOD/SCID recipients. e, RT-PCR analysis for PDX-1 expression the pancreas of NOD/SCID recipients. GFP+ donor cells did not express PDX-1.

As shown in a representative example, both purified and unpurified BM derived cells contributed to chimerism in the BM as expected, but also engrafted the damaged pancreas of STZ treated recipients (FIG. 2g). Donor reconstituted mice contained T, NK, macrophage and granulocytic donor (GFP+) cells, whereas mature hematopoietic cells from the donor were absent in the pancreas, despite the presence of an average of 14.4% GFP+ donor derived BM cells (FIG. 2g). Irradiated untreated mice showed less than 0.5±0.2% of donor GFP cells (n=11, data not shown). Frequency of donor chimerism in either pancreas or BM, as measured by the percentage of GFP+ cells detected in transplanted diabetic mice, was related to observed reductions in blood glucose (FIGS. 3h and i). The level of donor engraftment in the pancreas did not correlate with decreased blood glucose (R=0.51); however, reconstitution of the BM compartment with donor cells was directly related to corrected hyperglycemia (R=0.92). Since in vitro cultures of cell types have been shown to induce insulin secretion in high glucose containing conditions (19,20), the inventor sought to determine whether transplantation of BM cells into hyperglycemic environments were able to induce BM cells to produce insulin in vivo. As shown in a representative example, mononuclear cells from the BM of engrafted mice were devoid of insulin expression (FIG. 2h, inset) suggesting that donor BM cells were not providing insulin in rescued mice.

Due to the absence of mature hematopoietic marker expression in the pancreas of rescued hyperglycemic mice, the inventor analyzed pancreatic sections of diabetic mice by immunohistochemistry. As indicated by H+E staining, donor GFP+ cells were detected specifically in both the ductal (No.1) and surrounding islets regions (No.2) (FIG. 3a). Staining with insulin specific antibodies revealed that the majority of BM derived GFP+ cells were devoid of insulin secretion in either pancreatic site; however, a low frequency of donor BM derived cells (GFP+) also co-expressed insulin (indicated by arrows, FIG. 3a, GFP/Insulin panels). To further explore the validity of detecting insulin producing BM derived cells, single cells were analyzed by confocal laser scanning microscopy (FIG. 3b), and in depth z-series image analysis to assure intact insulin producing cells were being identified (FIG. 3c). In a representative example, subcellular localization of GFP protein was observed in both nuclear and cytoplasmic compartments, whereas insulin was found exclusively in the cytoplasm and not in 4,6 diamidino-2-phenylindole (DAPI) stained nuclei (Blue, FIG. 3b). Using fixed x and y coordinates, incremental z-series images indicated that single GFP+ cells expressed insulin were detectable in the same plane as insulin protein (FIG. 3c). In addition, insulin staining followed a punctate pattern, suggestive of organized insulin production in cytoplasmic vesicles (arrows, FIG. 3c). These observations are analogous to previous reports demonstrating the ability of BM derived regeneration initiating cells to adopt alternative tissue phenotypes upon transplantation, thereby identifying cells with displaying transdifferentiation properties.

By demonstrating the potential of mammalian cells to spontaneously fuse and adopt dual phenotypes of mixed cell populations, an alternative explanation to observed transdifferentiation properties of adult regeneration initiating cells has been provided (21,22). To date, cellular fusion has not been examined using in vivo transplantation models that have observed potential transdifferentiation (23). Nevertheless, the explanation of spontaneous fusion does not account for the few reports that demonstrate physiological restoration of tissue function after transplantation of "transdifferentiating" BM derived regeneration initiating cells. To contribute to the resolution of this issue using the inventor's model, the inventor quantitatively compared the frequency of donor GFP+ BM cells capable of co-expressing insulin in the pancreas of transplanted mice treated or not treated with STZ (FIG. 3d). GFP+ cells that co-express insulin were absent in non-diabetic mice transplanted with BM cells, whereas a frequency of 2.5% of all insulin positive cells in the pancreas of rescued diabetic animals were of donor origin (GFP+/Insulin+). The presence of insulin expressing donor cells was only observed in mice treated with STZ, suggesting that pancreatic damage was required to induce this phenotype. To determine whether insulin positive cells derived from BM have undergone normal differentiation associated with beta cell differentiation, donor GFP+ and GFP− recipient cells were isolated from the pancreas of rescued diabetic mice and analyzed for the expression of the transcription factor, PDX-1. PDX-1 expression has been shown to be essential for the induction of beta cell fate during embryonic and adult islet cell differentiation (24). To date, molecular determinants of cell fate have yet to be evaluated in observed transdifferentiating progeny (25). Recipient GFP-pancreatic cells showed expression of PDX-1, indicative of active islet regeneration, whereas donor GFP+ cells derived from the BM were devoid of PDX-1 expression (FIG. 3e). Both populations expressed the house keeping gene, beta actin. Differential expression of PDX-1 suggests that although BM derived cells were capable of adopting islet cell phenotype (insulin production), they do not appear to demonstrate cellular differentiation process previously associated with beta cell development (26). The results demonstrate that insulin positive BM derived regeneration initiating cells are detected preferentially in the damaged pancreas of diabetic mice (FIG. 3d), and may represent transdifferentiation of BM regeneration initiating cells or cellular fusion events occurring in vivo. More importantly, irrespective of the mechanism and origin from which these cells arise, the low frequency of these insulin producing BM derived cells suggests they are unable to account for the marked increase in serum insulin and physiological correction of hyperglycemia in transplanted recipients (FIGS. 2a-f).

Figure 4:
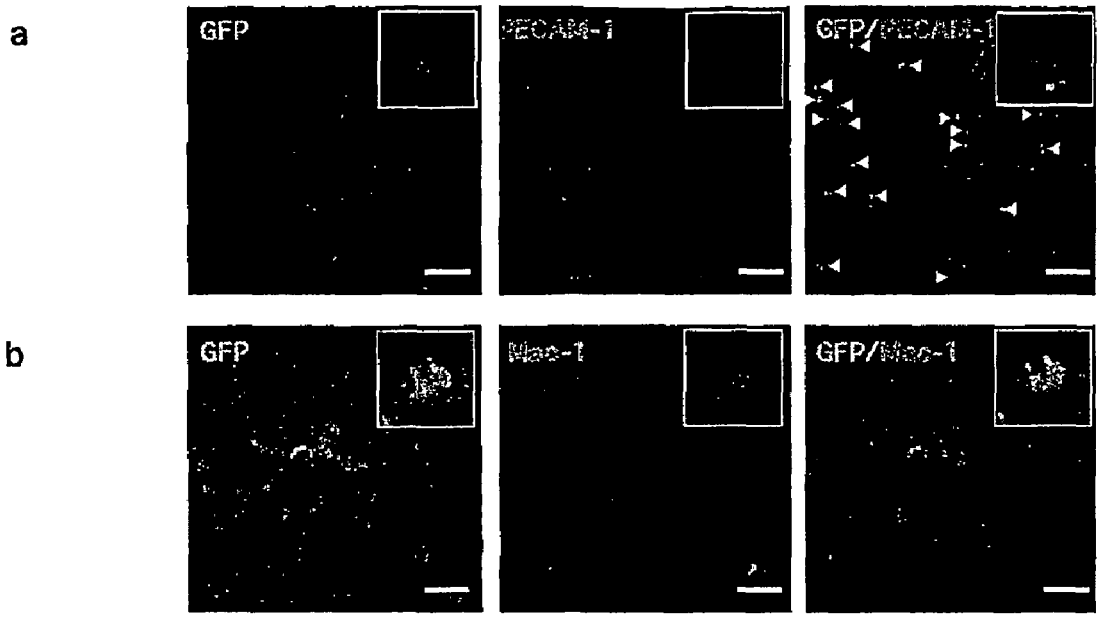
FIG. 4 shows that GFP$^+$ donor cells in the pancreas of recipient NOD/SCID mice co-express PECAM-1 and promote the production of recipient-derived insulin producing cells. a, GFP$^+$ donor cells in the pancreas of recipient NOD/SCID mice express the endothelial cell marker PECAM-1. Arrowheads and inset indicate GFP+/PECAM-1$^+$ cells. b, GFP$^+$ donor cells in the pancreas of recipient NOD/SCID mice do not express the monocyte and macrophage marker Mac-1. Insets indicate GFP$^+$/Mac-1$^+$ cells found in the pancreas of STZ-treated GFP/FVB mice. c, Frequency of PECAM-1$^+$ donor endothelial cells in the chimeric pancreas of NOD/SCID recipients. d, e, Analysis of the number of islets and the number of insulin producing cells in the pancreas of STZ-treated NOD/SCID recipients.
Figure 4:
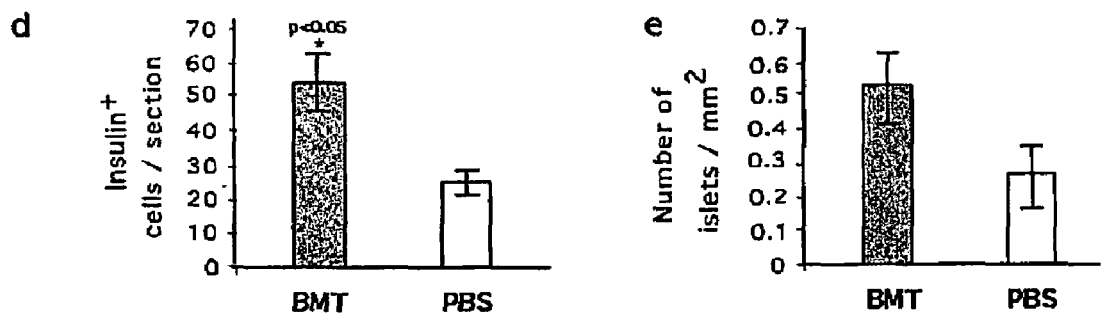

The cellular process of regenerative tissue repair in the adult has been thought to be comparable to organogenesis in the developing embryo (27). In the case of pancreatic development, the invagination of mesenchymal cells allows the initial emergence of pancreatic tissue by interaction with endothelium and subsequent islet neogenesis (28). Recent evidence indicates that the endothelial interaction is critical for pancreatic beta cell development (29). Based on the essential role of endothelium in islet and beta cell development, the pancreas of rescued diabetic mice were examined for the presence of endothelial cells. Although recipient endothelial cells, identified by expression of the endothelial marker PECAM-1 (platelet/endothelial cell adhesion molecule-1) (29,30), could be identified in regenerative pancreatic sections (GFP−/PECAM-1+), a large proportion of endothelial cells were of donor (GFP+/PECAM-1+) origin (FIG. 4a, arrows). Magnified image of GFP+ and PECAM-1+ detection of single donor cells is shown (FIG. 4a, inset). Despite the absence of mature hematopoietic cells in the pancreas of engrafted mice (FIG. 2f), pancreas sections were also counterstained with MAC-1 specific antibodies to assure the absence false positive endothelial cell identification. All sections were devoid of MAC-1 positive cells (FIG. 4b). Insets show GFP+ macrophage isolated from the BM of GFP transgenic mice as positive staining controls. The number of endothelial (PECAM-1+) positive BM derived cells detected in mice transplanted with purified or unpurified BM cells was compared between STZ treated or untreated recipient mice (FIG. 4c). As many as 9.2% of donor BM derived cells engrafting ductal or surrounding islet regions were of the endothelial lineage (GFP+/PECAM-1+), in contrast to untreated transplanted mice that were devoid of donor endothelial cells.

Since the majority of insulin producing cells in the pancreas of rescued diabetic mice were not of donor origin (Insulin+/GFP-, FIG. 3d), and donor endothelial cell engraftment was detected in recipient pancreatic tissue, the inventor investigated whether the source of serum insulin and normalized blood glucose was arising from an endogenous source. Quantitative histomorphormetric analysis indicated that the total number of islets (expressed per $mm^2$) in mice transplanted with BM was greater than hyperglycemic mice transplanted with PBS or irradiated BM (FIG. 4d). Moreover, the number of insulin positive cells per section was higher in transplanted mice compared to PBS or irradiated BM transplanted controls (FIG. 4e). Identification of donor endothelial cell engraftment in both ductal and surrounding islet regions, combined with increased number of insulin producing cells suggests that physiological rescue of hyperglycemia coincides with regeneration of recipient islets. Aside from the low frequency of donor cells adopting islet phenotypes, the results reveal a novel cellular mechanism by which transplantation of BM derived regeneration initiating cells contribute to tissue regeneration and restoration of organ function.

To examine the cellular mechanism by which BM derived regeneration initiating cells are capable of initiating recipient pancreatic regeneration, the pancreata of STZ-induced diabetic mice transplanted with either purified BM cells or PBS were analyzed 4 (Day 14) and 7 (Day 17) days post transplantation for endothelial cell engraftment and insulin production at the onset of blood glucose correction (FIG. 5a). As early as 4 days post BM transplantation, donor GFP+ cells engrafted surrounding areas of the pancreatic ducts and within recipient islets (FIG. 5b). Only islet regions contained insulin expressing cells, whereas no insulin producing cells were observed in ductal regions (FIG. 5b). By Day 17, ductal and islet sites were surrounded by larger numbers of BM derived donor cells (FIG. 5c). Islet structures in BM transplanted mice contained greater numbers of insulin producing cells (FIG. 5c), in contrast to diabetic mice transplanted with PBS that contained few islets and only residual insulin expressing cells (FIG. 5d). At Day 14, quantitative analysis of pancreatic tissue sections indicated that there was no statistical difference in the number of insulin producing cells or number of total islets between diabetic recipients transplanted with BM or PBS, whereas by Day 17, significantly greater numbers of insulin producing islet structures were observed in BM transplanted recipients only (FIGS. 5e and f). Donor derived GFP+ cells capable of expressing insulin were not detectable at either Day 14 or 17, suggesting that insulin producing BM derived cells (phenotypically transdifferentiating cells) detected at Day 42 (FIGS. 3b and c) arise only after prolonged periods in vivo (FIG. 5e). Since elevated blood glucose was reduced by Day 17, and donor GFP+/Insulin+ cells were not observed at this time, it was suggested that BM derived transdifferentiating cells do not contribute to the onset of glucose control.

At Day 14, the concentration and total pancreatic insulin were similar in BM and PBS transplanted mice, whereas by Day 17, diabetic recipients transplanted with BM showed marked increases in insulin content (FIGS. 5g and h, dotted horizontal line indicates insulin level at Day 10 prior to IV transplantation). This increase in insulin producing cells and pancreatic regeneration observed at Day 17 correlated with significant reductions ($p<0.001$) in blood glucose levels (16.5±1.1 mmol/l, n=7) as compared to PBS transplanted mice that remained hyperglycemic (29.8±1.2 mmol/l, n=6), whereas no statistical difference in blood glucose was observed in BM vs PBS transplanted recipients at Day 14 (20.7±2.5 vs 28.6±4.6 respectively). Further analysis of the pancreata of BM transplanted mice indicated that donor derived endothelial (GFP+/PECAM-1+) cells were detectable in both ductal and islet regions at 4 and 7 days post transplantation (FIGS. 5i and j). In contrast to Day 14 (FIG. 5k), quantitative analysis of the frequency of donor derived endothelial cells in the pancreas demonstrated a direct correlation between endothelial engraftment and reduction of blood glucose by Day 17 (r=0.96, FIG. 5l). The results indicate that a rapid regeneration of insulin producing cells arising within islet structures occurs within 4-7 days post transplantation of BM derived cells, thereby providing an endogenous source of pancreatic insulin capable of reducing blood glucose levels in diabetic recipients. The engraftment of BM derived endothelial cells strongly correlates with the rapidity of recipient pancreatic islet regeneration, resulting in reductions in blood glucose.

Figure 5:
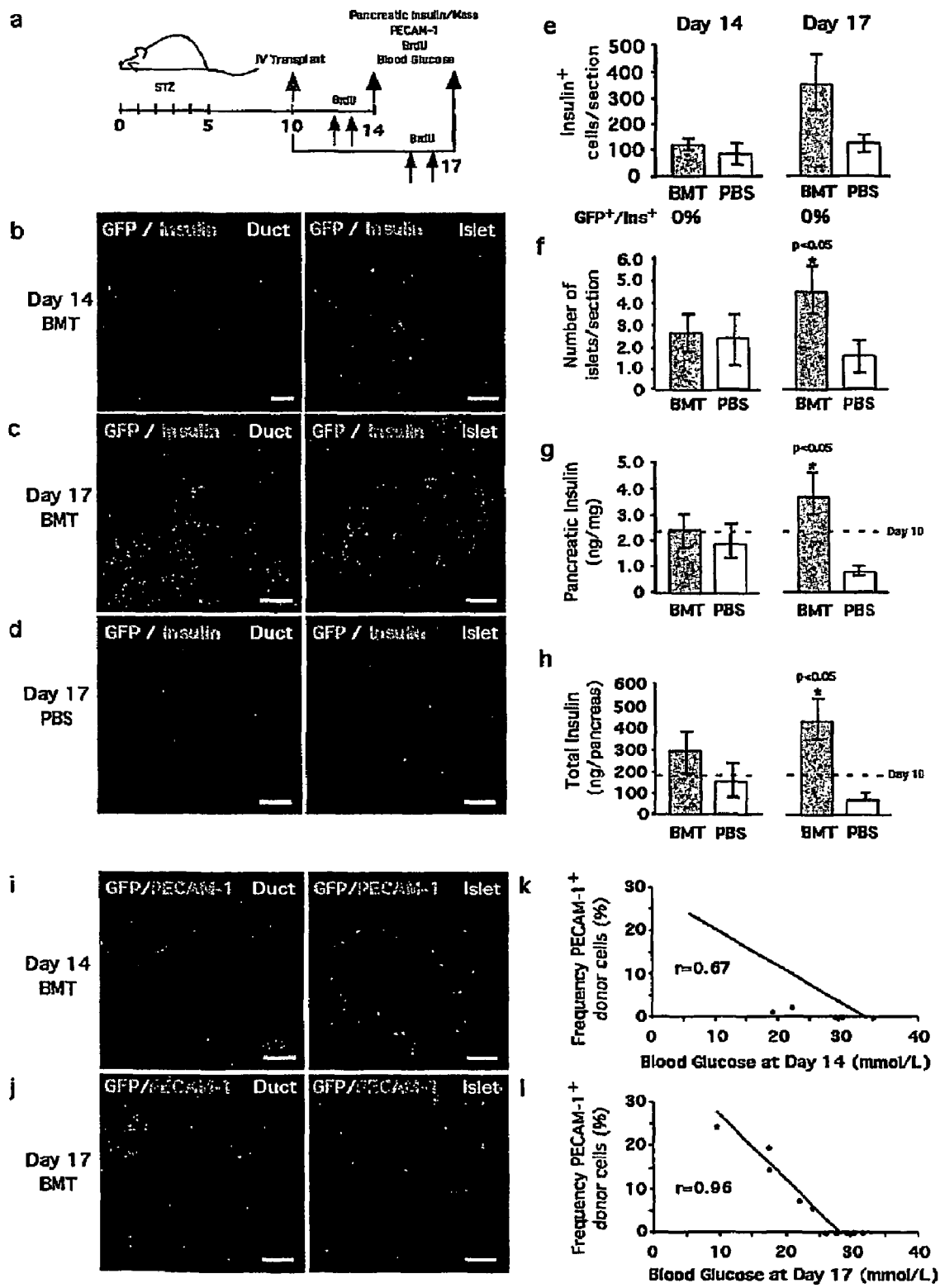
FIG. 5 shows that PECAM-1 expressing donor BM derived stem cells engraft pancreas of recipient mice and correlate with rapid pancreatic insulin production. a, Experimental design for the detection of insulin producing cells, PECAM-1 expressing donor cells and BrdU labeled proliferating cells in the pancreas of hyperglycemic mice 4 and 7 days after transplant with GFP+ BM cells or mock transplanted with PBS. b-d, Representative analysis of GFP and insulin expressing cells detected in pancreatic ductal and islets regions at 4 and 7 days post IV transplantation of either BM or PBS. e,f, Quantitative analysis of the number of insulin producing cells and the number of islet structures per section in the pancreas of STZ treated mice, 4 and 7 days post transplantation with either BM or PBS. Horizontal dotted line indicates levels at Day 10 prior to transplantation. g,h, Quantitative analysis of the pancreatic mass and total pancreatic insulin content in STZ-treated mice 4 and 7 days after BM transplant or PBS injection. All data are shown as mean±S.E.M. (n=4 mice per group). A significant (p<0.05) increase in pancreas insulin content was observed in BM transplanted mice within 7 days. Horizontal dotted line indicates levels at Day 10 prior to transplantation. i,j, Representative analysis of PECAM-1 expressing GFP+ donor cells surrounding pancreatic structures 4 and 7 days post transplantation. Arrowheads represent double stained GFP+/PECAM-1+ cells. All scale bars=50 µm. k,l Correlation of early blood glucose correction with the frequency of PECAM-1+ donor cells in the pancreas recipient mice sacrificed 4 days (n=6), and 7 days (n=11) after BM cell or PBS IV transplantation.
Figure 6:
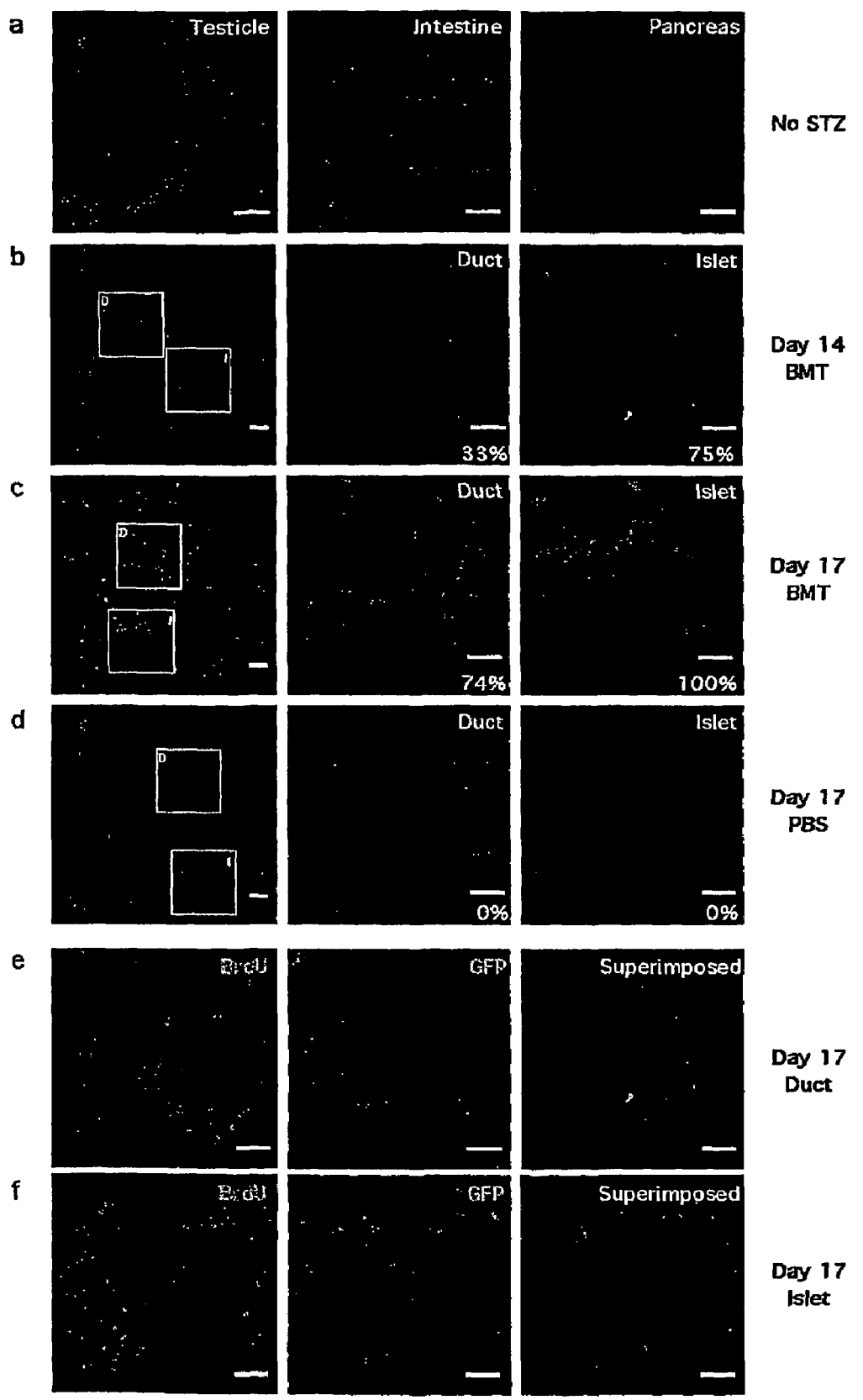
FIG. 6 shows that the presence of GFP+ donor cells in the pancreas of transplanted recipient mice promotes the proliferation of endogenous cells in the ductal and pancreatic islet regions. a, Visualization of BrdU-labeled proliferating cells in the testicle, intestine, and pancreas of NOD/SCID mice not injected with STZ. b-d, Visualization of BrdU-labeled proliferating cells in the ductal (D) and islet (I) regions of the pancreas of STZ-treated mice, 4 and 7 days post BM or PBS transplantation. e,f, Serial pancreatic sections were either stained for BrdU, or left unstained for detection of GFP, and were then superimposed to indicate the presence of recipient vs donor derived proliferating cells in the ductal and islet pancreatic structures. All scale bars=50 µm.

Recipient Cells Within Ductal and Islet Regions Proliferate in Response to Pancreatic Engraftment of Transplanted BM Derived Regeneration Initiating Cells Since STZ treatment eliminates insulin-producing cells prior to BM transplantation, and production of pancreatic insulin is recovered by the emergence of newly formed insulin producing cells by Day 17 (FIG. 5), the inventor surmised that cells within the recipient pancreas must proliferate rapidly to establish their newly generated pools of insulin expressing cells within 7 days. To determine the presence and origin of proliferating pancreatic cells that allow generation of beta cells, hyperglycemic mice transplanted at Day 10 with either BM or PBS were given 2 single injections of BrdU at 50 ug/kg body weight and sacrificed at Day 14 or Day 17 for analysis of proliferating cells incorporating this nucleotide (FIG. 5a). To determine the normal homeostatic turnover of pancreatic cells in recipients, untreated NOD/SCID mice were injected with BrdU and examined for the presence of proliferating cells (FIG. 6a). Unlike tissue known to undergo continual renewal, such as the testis and intestine, undamaged pancreas of normoglycemic mice contained nearly undectable numbers of proliferating (BrdU+) cells (FIG. 6a), suggesting that under normal physiological conditions the pancreas is not capable of a high frequency of cellular turnover. In contrast, by Day 14, the damaged pancreata of STZ induced diabetic mice that were transplanted with BM derived cells contained proliferating cells in both ductal and islet sites, which further increased by Day 17 (FIGS. 6b and c). The proportion of total ductal and islet structures containing proliferating cells was quantitated (FIGS. 6b and c, bottom right of panels). At Day 14, appropriately 33% of all ductal structures contained cells undergoing cell division, whereas as many as 75% of islet structures contained proliferating cells (FIG. 6b). By Day 17, the proportion of proliferating ductal sites increased to 74%, whereas all islet structures observed contained proliferating cells (FIG. 6c). In contrast, the pancreas of diabetic mice transplanted with PBS possessed no proliferating cells in either ductal or islet structures at Day 14 (data not shown) or Day 17 (FIG. 6d).

Since transplantation of irradiated BM cells was unable to rescue hyperglycemia (FIG. 2b), it was predicted that proliferating (BrdU+) donor BM cells may account for the proliferating cells observed in the ductal and islets sites of transplanted mice. To examine the origin of proliferating cells observed in the pancreas of recipient mice, serial 5 mM sections of ductal and islets tissue were stained with BrdU antibody and the following section examined for donor derived GFP+ cells. These sequential sections were compared independently and also superimposed to identify the number of donor proliferating cells (BrdU+/GFP+). Simultaneous BrdU+ and GFP+ cells cannot be visualized on the same tissue section since acid treatment required for denaturation of DNA during BrdU staining destroys fluorescent properties of GFP. Of the proliferating (BrdU+) cells surrounding the pancreatic ductal regions of BM transplanted mice, the majority of proliferating cells did not co-localize with GFP+ donor cells as determined by either direct side by side comparison of sequential sections or by identification of BrdU+/GFP+ (yellow) cells upon superimposing serial images (FIG. 6e). Proliferating BrdU+ cells found in the islet regions contained few, although a greater proportion of BrdU+/GFP+ BM derived donor cells than the ductal regions (FIG. 6f). Based on this analysis, the results indicate that the majority of proliferating cells in the ductal and islet regions are of recipient origin. The inventor suggest that regeneration of pancreatic structures leading to production of insulin expressing cells is a function of endogenous cell proliferation and differentiation initiated by transplantation and engraftment of BM derived regeneration initiating cells.

Recent excitement in the area of tissue repair has focused on the transdifferentiation potential of regeneration initiating cells observed after transplantation (14,25,27). The recovery of cardiac stroke volume after myocardial infarction (7), and recovery of enzymatic production of liver enzymes in FAH null mice (6), have suggested that transdifferentiating BM derived regeneration initiating cells are capable of providing a physiological benefit to recipients. However, the inability of the low frequency of transdifferentiating regeneration initiating cells to account for functional restoration of recipients tissue, has suggested that alternative mechanisms may be present. The present invention provides a novel mechanism by which BM derived cells may contribute to tissue/organ repair by participating in endogenous regeneration. Therefore the use of BM transplantation is a feasible approach to manage patients with pancreatic tissue damage and that may also provide a means to assist in the regenerative process of other tissue types.

Example 2

Human Regeneration Initiating Cells

Figure 7:
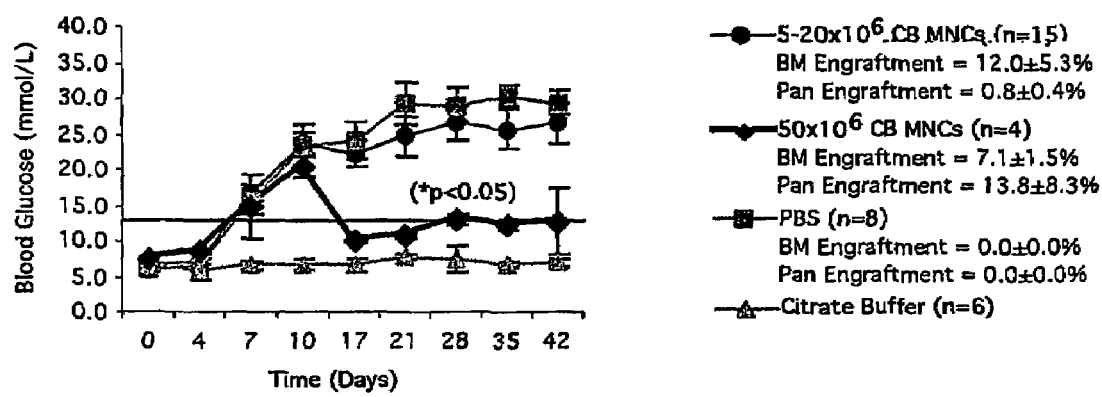
FIG. 7 shows that intravenous transplantation of human cord blood mononuclear in recipient NOD/SCID mice treated with streptozotocin (STZ). A) Recipient mice treated with STZ were IV transplanted with human CB cells at Day 10 with low and high doses. Low doses ranged between 5-20 million mononuclear cells, and high dose was equal to 50 million mononuclear cells. At low doses of transplanted cells, STZ treated mice, induced to become hyperglycemic, did not alter their serum glucose levels out to Day 42. At high dose of CB cells, transplanted mice treated with STZ demonstrated a rapid reduction in blood glucose levels unlike low dose CB transplanted mice or mice transplanted with PBS. Control mice not treated with STZ, but receiving carrier citrate buffer used to resuspend STZ retained normal levels of glucose during the experimental period. (n=4-8)B) Levels of human cells in both bone marrow (BM) and pancreas of recipient STZ treated mice transplanted with human CB were evaluated. Level of human engraftment in the BM of recipient mice is indicative of hematopoietic stem cell (HSC) function, whereas level of engraftment in the pancreas is indicative of RIC function. At low dose, levels of human cells engrafting the BM site were considerably higher than levels in the pancreas and no reduction of hyperglycemia was demonstrated (see A above). In contrast, STZ treated mice transplanted with high dose CB cells showed a higher level of human cell engraftment in the pancreas, as oppose to the BM site. Since the level of human engraftment in the BM did not differ between low and high doses, but the level of pancreas engraftment in high dose was much higher than in low dose, the frequency of human RICs differs from the frequency of human HSCs, suggesting that these human RICs are biologically distinct from human HSCs. Each symbol indicates individual mice transplanted at doses and tissue indicated.
Figure 7:
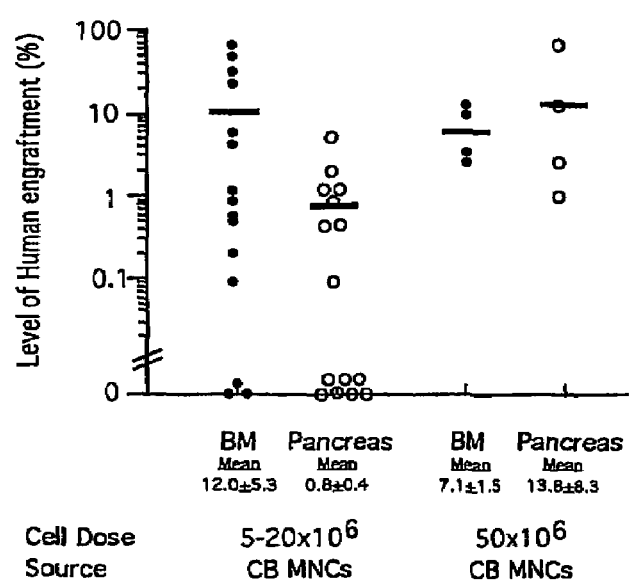

The isolated mononuclear cells from the human CB were transplanted intravenously into recipient NOD/SCID mice treated with streptozotozin. The LDMNCs were insolated by gradient centrifugation using Ficoll-pague (Pharmacia, USA). The mice were either transplanted with high or low doses of the mononuclear cells. As is shown in FIG. 7, in mice receiving $5\text{-}20 \times 10^6$ mononuclear cells there was engraftment of the cells in the bone marrow but not in the pancreas. In contrast, when mice receive $50 \times 10^6$ mononuclear cells there was engraftment of both bone marrow and the pancreas. At low doses of the mononuclear cells, no reduction in hyperglycemia was demonstrated although it was demonstrated at the higher dose. It is expected that the different observations at high and low doses are due to the fact that the regeneration initiation cells occur at a low frequency and therefore their effect is demonstrated only at higher doses. In contrast, hematopoietic stem cells occur at a higher frequency and account for the bone marrow engraftment seen at the lower doses. Consequently, the results demonstrate that the regeneration cells are biologically distinct from hematopoietic stem cells.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

1. Bjornson, C. R., Rietze, R. L., Reynolds, B. A., Magli, M. C. & Vescovi, A. L. Turning brain into blood: a hematopoietic fate adopted by adult neural stem cells in vivo. Science 283, 534-7. (1999).
2. Ferrari, G. et al. Muscle regeneration by bone marrow-derived myogenic progenitors. Science 279, 1528-30. (1998).
3. Gussoni, E. et al. Dystrophin expression in the mdx mouse restored by stem cell transplantation. Nature 401, 390-4. (1999).
4. Jackson, K. A., Mi, T. & Goodell, M. A. Hematopoietic potential of stem cells isolated from murine skeletal muscle. Proc Natl Acad Sci USA 96, 14482-6. (1999).
5. Krause, D. S. et al. Multi-organ, multi-lineage engraftment by a single bone marrow-derived stem cell. Cell 105, 369-77. (2001).
6. Lagasse, E. et al. Purified hematopoietic stem cells can differentiate into hepatocytes in vivo. Nat Med 6, 1229-34. (2000).
7. Orlic, D. et al. Bone marrow cells regenerate infarcted myocardium. Nature 410, 701-5. (2001).
8. Blau, H. M. et al. The evolving concept of a stem cell: entity or function? Cell 105, 829-41. (2001).
9. Rossant, J. Stem cells from the Mammalian blastocyst. Stem Cells 19, 477-82. (2001).
10. Odorico, J. S., Kaufman, D. S. & Thomson, J. A. Multi-lineage differentiation from human embryonic stem cell lines. Stem Cells 19, 193-204. (2001).
11. Orkin, S. H., Zon, L. I., Odorico, J. S., Kaufman, D. S. & Thomson, J. A. Hematopoiesis and stem cells: plasticity versus developmental heterogeneity. Nat Immunol 3, 323-8. (2002).
12. Tisdale, J. F., Dunbar, C. E., Odorico, J. S., Kaufman, D. S. & Thomson, J. A. Plasticity and hematopoiesis: Circe's transforming potion? Curr Opin Hematol 9, 268-73. (2002).
13. Brazelton, T. R., Rossi, F. M., Keshet, G. I. & Blau, H. M. From marrow to brain: expression of neuronal phenotypes in adult mice. Science 290, 1775-9. (2000).
14. Springer, M. L., Brazelton, T. R., Blau, H. M., Rossi, F. M. & Keshet, G. I. Not the usual suspects: the unexpected sources of tissue regeneration. J Clin Invest 107, 1355-6. (2001).
15. Zysset, T. & Sommer, L. Diabetes alters drug metabolism—in vivo studies in a streptozotozin-diabetic rat model. Experientia 42, 560-2. (1986).
16. Quesenberry, P. et al. Studies on the regulation of hemopoiesis. Exp Hematol 13, 43-8. (1985).
17. Nakauchi, H., Sudo, K. & Ema, H. Quantitative assessment of the stem cell self-renewal capacity. Ann NY Acad Sci 938, 18-24; discussion 24-5. (2001).
18. Ortiz, M. et al. Functional characterization of a novel hematopoietic stem cell and its place in the c-Kit maturation pathway in bone marrow cell development. Immunity 10, 173-82. stem cells. (1999).
19. Yang, L. et al. In vitro trans-differentiation of adult hepatic stem cells into pancreatic endocrine hormone-producing cells. Proc Natl Acad Sci USA 99, 8078-83. (2002).
20. Lumelsky, N. et al. Differentiation of embryonic stem cells to insulin-secreting structures similar to pancreatic islets. Science 292, 1389-94. (2001).
21. Ying, Q. L., Nichols, J., Evans, E. P. & Smith, A. G. Changing potency by spontaneous fusion. Nature 416, 545-8. (2002).
22. Terada, N. et al. Bone marrow cells adopt the phenotype of other cells by spontaneous cell fusion. Nature 416, 542-5. (2002).
23. McKay, R., Nakauchi, H., Sudo, K. & Ema, H. A more astonishing hypothesis. Nat Biotechnol 20, 426-7. (2002).
24. Shih, D. Q. et al. Profound defects in pancreatic beta-cell function in mice with combined heterozygous mutations in Pdx-1, Hnf-1alpha, and Hnf-3beta. Proc Natl Acad Sci USA 99, 3818-23. (2002).
25. Tsai, R. Y. et al. Plasticity, niches, and the use of stem cells. Dev Cell 2, 707-12. (2002).
26. Sander, M. & German, M. S. The beta cell transcription factors and development of the pancreas. J Mol Med 75, 327-40. (1997).
27. Weissman, I. L., Sander, M. & German, M. S. Stem cells: units of development, units of regeneration, and units in evolution. Cell 100, 157-68. (2000).
28. Grapin-Botton, A., Melton, D. A., Sander, M. & German, M. S. Endoderm development: from patterning to organogenesis. Trends Genet 16, 124-30. (2000).
29. Lammert, E., Cleaver, O. & Melton, D. Induction of pancreatic differentiation by signals from blood vessels. Science 294, 564-7. (2001).
30. Takakura, N. et al. A role for hematopoietic stem cells in promoting angiogenesis. Cell 102, 199-209. (2000).
31. Hattori, K. et al. Placental growth factor reconstitutes hematopoiesis by recruiting VEGFR1(+) stem cells from bone-marrow microenvironment. Nat Med 8, 841-9 (2002).
32. Heissig, B. et al. Recruitment of stem and progenitor cells from the bone marrow niche requires mmp-9 mediated release of kit-ligand. Cell 109, 625-37. (2002).
33. Bahary, N. & Zon, L. I. Development. Endothelium—chicken soup for the endoderm. Science 294, 530-1. (2001).
34. Peshavaria, M. & Pang, K. Manipulation of pancreatic stem cells for cell replacement therapy. Diabetes Technol Ther 2, 453-60. (2000).
35. Edlund, H. Pancreatic organogenesis-developmental mechanisms and implications for therapy. Nat Rev Genet 3, 524-32. (2002).
36. Peters, J., Jurgensen, A. & Kloppel, G. Ontogeny, differentiation and growth of the endocrine pancreas. Virchows Arch 436, 527-38. (2000).
37. Tsirigotis, M. et al. Analysis of ubiquitination in vivo using a transgenic mouse model. Biotechniques 31, 120-6. (2001).
38. Bhardwaj, G. et al. Sonic hedgehog induces the proliferation of primitive human hematopoietic cells via BMP regulation. Nat Immunol 2, 172-80. (2001).
39. Burkart, V. et al. Mice lacking the poly(ADP-ribose) polymerase gene are resistant to pancreatic beta-cell destruction and diabetes development induced by streptozocin. Nat Med 5, 314-9. (1999).
40. Ikehara S, Ohtsuki H, Good R A, Asamoto H, Nakamura T, Sekita K, Muso E, Tochino Y, Ida T & Kuzuya H, et al. Prevention of type I diabetes in nonobese diabetic mice by allogenic bone marrow transplantation. PNAS 82(22) 7743-7. 1985.
41. Than S, Ishida H, Inaba M, Fukuba Y, Seino Y, Adachi M, Imura H, & Ikehara S. Bone marrow transplantation as a strategy for treatment of non-insulin-dependent diabetes mellitus in KK-Ay mice. J. Exp. Med. 176(4), 1233-1238. (1992).
42. Bhatia M, Wang J C, Kapp U et al. Purification of primitive human hematopoietic cells capable of repopulating immune-deficient mice. Proc Natl Acad Sci USA 1997; 94:5320-5325.
43. Grewal S. S. et al. Unrelated donor hematopoietic cell transplantation: marrow or umbilical cord blood? Blood 101, 4233-4244. (2003).

I claim:

1. A method of treating pancreatic damage comprising administering isolated regeneration initiating cells to an animal in need thereof, wherein the regeneration initiating cells have the surface marker c-kit and at least one of CD34 and AC133.

2. The method according to claim 1 wherein the regeneration initiating cells are derived from a source selected from the group consisting of bone marrow, peripheral blood, umbilical cord blood or placenta.

3. The method according to claim 2 wherein the regeneration initiating cell has at least one additional marker selected from the group consisting of KDR, Tie-1/2, Tek-1/2, VEGF-receptor families, CD31, and angiopoietin receptors.

4. The method according to claim 1 wherein the regeneration initiating cell is human.

5. The method according to claim 1 for the treatment of Diabetes.

6. The method according to claim 5 wherein the diabetes is non-insulin dependent Type II diabetes.

7. The method according to claim 1 wherein said animal is a human.

8. The method according to claim 1 wherein the cells are low density mononuclear lymphocytes.

9. The method according to claim 1 for the treatment of hyperglycemia.

* * * * *

```
                        SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: PDX-1- Forward PCR Primer

<400> SEQUENCE: 1
ccacacagct ctacaaggac c                                              21

<210> SEQ ID NO 2
<211> LENGTH: 22
<212> TYPE: DNA
<213> ORGANISM: Artificial Sequence
<220> FEATURE:
<223> OTHER INFORMATION: PDX-1-Reverse PCR Primer

<400> SEQUENCE: 2
```

```
cgttgtcccg ctactacgtt tc                                              22

<210> SEQ ID NO 3
<211> LENGTH: 20
<212> TYPE: DNA
<213> ORGANISM: Artificial Sequence
<220> FEATURE:
<223> OTHER INFORMATION: beta actin-P1 PCR primer

<400> SEQUENCE: 3
gatccacatc tgctggaagg                                                 20

<210> SEQ ID NO 4
<211> LENGTH: 18
<212> TYPE: DNA
<213> ORGANISM: Artificial Sequence
<220> FEATURE:
<223> OTHER INFORMATION: beta actin-P2 PCR primer

<400> SEQUENCE: 4
aagtgacgtt gacatccg                                                   18
```